(12) United States Patent
Vitale et al.

(10) Patent No.: US 11,134,218 B2
(45) Date of Patent: *Sep. 28, 2021

(54) SECURE TELECONFERENCE MANAGEMENT

(71) Applicant: CAREGILITY CORPORATION, Eatontown, NJ (US)

(72) Inventors: John Mitchell Vitale, Mooresville, NC (US); David Walter Galas, Jackson, NJ (US); Jennifer R. Schell, Colts Neck, NJ (US); Philip Brock Purpura, Red Bank, NJ (US); Luke Brown, Philadelphia, PA (US)

(73) Assignee: CAREGILITY CORPORATION, Eatontown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/072,161

(22) Filed: Oct. 16, 2020

(65) Prior Publication Data

US 2021/0120210 A1 Apr. 22, 2021

Related U.S. Application Data

(63) Continuation of application No. 16/507,605, filed on Jul. 10, 2019, now Pat. No. 10,545,713, which is a (Continued)

(51) Int. Cl.
*H04N 7/15* (2006.01)
*H04M 3/56* (2006.01)
(Continued)

(52) U.S. Cl.
CPC ............ *H04N 7/155* (2013.01); *H04M 3/563* (2013.01); *G06F 3/033* (2013.01); *G16H 10/60* (2018.01);
(Continued)

(58) Field of Classification Search
CPC .... H04N 7/155; H04N 5/23299; H04N 7/147; H04N 5/23296; H04M 3/563;
(Continued)

(56) References Cited

U.S. PATENT DOCUMENTS 8,375,421 B1 2/2013 Shigapov et al.
9,585,185 B1 2/2017 Sapkota et al.
(Continued)

*Primary Examiner* — Melur Ramakrishnaiah
(74) *Attorney, Agent, or Firm* — BakerHostetler

(57) ABSTRACT

A secure teleconference with a patient treatment room may be initiated by receiving, at a central facility, a request for a conference from a clinician application, and then identifying a virtual meeting room and sending an identifier for a conference to the treatment room. The conference is then be established by receiving a call at the central facility from the treatment room, where the call identifies the conference. The central facility then joins the treatment room and the clinician application to the virtual meeting room. Teleconferences may thus be established without reference to sensitive patient information. For security, no incoming conferencing calls may be made to the treatment room directly, and virtual meeting rooms may be eliminated after single use. A call may further be initiated by receiving a request from the treatment room, e.g., which is processed by the central facility to alert one or more clinicians.

20 Claims, 5 Drawing Sheets

Related U.S. Application Data continuation of application No. 16/046,374, filed on Jul. 26, 2018, now Pat. No. 10,397,521.

(60) Provisional application No. 62/537,663, filed on Jul. 27, 2017.

(51) Int. Cl.
*G06F 3/033* (2013.01)
*H04N 5/232* (2006.01)
*G16H 80/00* (2018.01)
*H04N 7/14* (2006.01)
*G16H 10/60* (2018.01)

(52) U.S. Cl.
CPC ............ *G16H 80/00* (2018.01); *H04M 3/567* (2013.01); *H04M 2203/5009* (2013.01); *H04M 2203/6081* (2013.01); *H04N 5/23296* (2013.01); *H04N 5/23299* (2018.08); *H04N 7/147* (2013.01)

(58) Field of Classification Search
CPC .......... H04M 2203/5009; H04M 3/567; G06F 2203/04806; G06F 3/033; G16H 80/00; G16H 10/60

USPC ........................................... 348/14.01–14.16
See application file for complete search history.

(56) References Cited

U.S. PATENT DOCUMENTS

| | | | |
|---|---|---|---|
| 2002/0037074 A1* | 3/2002 | Dowens | G10L 13/00 379/88.14 |
| 2002/0122391 A1* | 9/2002 | Shalit | H04L 65/403 370/260 |
| 2005/0058088 A1* | 3/2005 | Decker | H04M 7/006 370/260 |
| 2008/0231460 A1 | 9/2008 | Owen et al. | |
| 2010/0118111 A1 | 5/2010 | Bouazizi | |
| 2011/0214074 A1* | 9/2011 | Pegg | G06Q 10/10 715/758 |
| 2012/0062689 A1* | 3/2012 | Sai | H04N 7/15 348/14.09 |
| 2013/0246084 A1 | 9/2013 | Parmanto et al. | |
| 2016/0103437 A1* | 4/2016 | Alfredsson | H04N 7/183 700/83 |
| 2016/0283665 A1 | 9/2016 | Sampath et al. | |
| 2017/0053085 A1 | 2/2017 | Bulat | |
| 2017/0078341 A1 | 3/2017 | Devinck et al. | |

\* cited by examiner

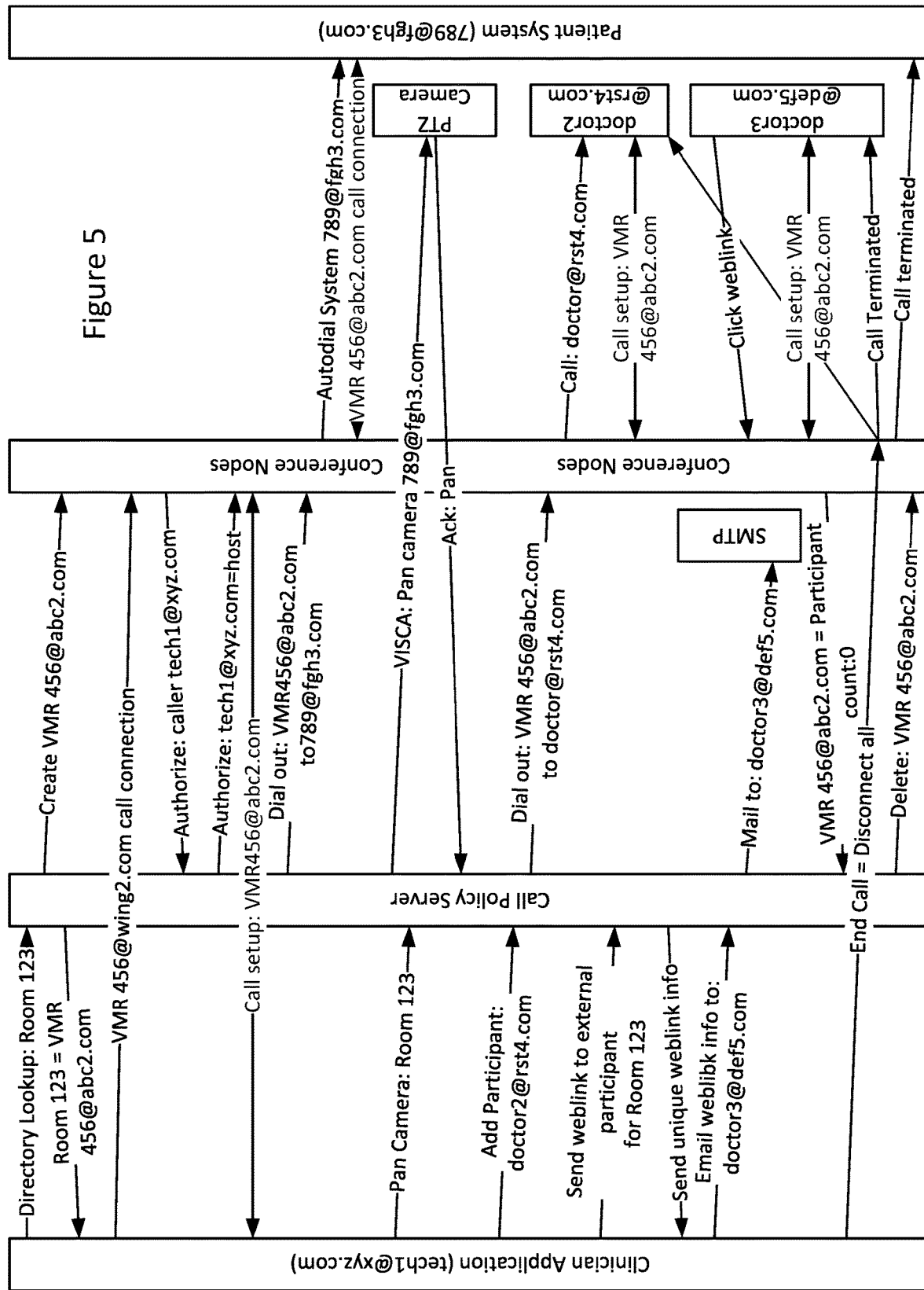

SECURE TELECONFERENCE MANAGEMENT

CROSS-REFERENCE TO RELATED APPLICATIONS

This application is a continuation of U.S. patent application Ser. No. 16/507,605, titled "Secure teleconference management," filed Jul. 10, 2019, which is a continuation of U.S. patent application Ser. No. 16/046,374, titled "Secure teleconference management," filed Jul. 26, 2018, and claims benefit of U.S. Provisional Patent Application Ser. No. 62/537,663 (Vitale, et al.), filed on Jul. 27, 2017, also titled "Secure teleconference management," the contents of which are hereby incorporated by reference in their entirety.

BACKGROUND

This disclosure pertains to video teleconferencing.

SUMMARY

Secure teleconferencing between a terminal and a remote application may be facilitated by call management system at a central facility, for example, which responds to a request for a conference from a remote application or from the terminal. When the central facility is satisfied by the credentials of the call initiator, a teleconference may be established by first sending a call invitation to the terminal, then receiving a call at the central facility from the terminal, where the call identifies the conference. The central facility may then join the terminal and the remote application to a virtual meeting room.

The terminal may be located in a patient treatment room, for example, and the remote application may be a clinician application.

Teleconferences may thus be established without reference to sensitive patient information, for example. For security, no incoming conferencing calls may be made to the treatment room directly, and virtual meeting rooms may be eliminated after single use.

A terminal may be adapted in number of ways to facilitate secure teleconferencing. For example, in addition to the security feature of not allowing incoming calls, a patient room terminal may be equipped with infrared equipment for nighttime or low-light observation. The terminal may be further adapted to allow certain operations for remote camera control, including, but not limited to, control the rate of changes to pan, tilt, or zoom, calibrating field of view, or using inverse gnomonic transformation to facilitate changes in pan, tilt, and zoom.

Similarly, a central facility or clinician application may be adapted to facilitate camera operations, such as controlling the rate of changes to pan, tilt, or zoom, calibrating field of view, or using inverse gnomonic transformation to facilitate changes in pan, tilt, and zoom. For example, user mouse operations may be used to trigger shifts in pan, tilt, and zoom. For example, an input for changing a field of view of a camera may be provided by a user clicking and holding on a position in an image of the current view. The system may use the X, Y coordinate clicked by the use to compute new pan, tilt, and zoom parameters. For example, clicking and holding may tri trigger an inverse gnomonic transformation to determine a new field of view and associated pan, tilt, and zoom coordinates. Such operations may be position sensitive, e.g., whereby the system response to clicking in one zone or position in an image has a different effect than does clicking in a different zone or position. Similarly, camera operations may be enhanced by storing pre-selected views or settings, for example. Camera instructions may be sent out of band of the teleconference.

The call management central facility may be arranged to provide for additionally joining unauthorized parties to the a call, e.g., by pre-arrangement or by request of an authorized clinician on a call, such that parties are given access to the virtual meeting room for the call without the parties having to provide security credentials to the call management system. This may be used, for example, to invite loved ones of patients or consulting clinicians to join in a teleconference in process.

The call management system may start a new virtual meeting room for each call or, for example, select a virtual meeting room from a set of pre-established call resources.

A treatment room terminal, call management system, or clinician application may be connected to a local station, such as a nurse's station, or a care management system providing patient care or information. For example, a call button associated with a treatment room terminal may both send a request for a teleconference to the call management system and alert a local nursing station. A clinician application may receive confidential patient medical data from a care management system, while the call management system has no such access. Conversely, the call management system may provide information about teleconferences to the care management system so that records of calls can be stored in a patient's medical records.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to limitations that solve any or all disadvantages noted in any part of this disclosure.

BRIEF DESCRIPTION OF THE FIGURES

A more detailed understanding may be had from the following description, given by way of example in conjunction with the accompanying drawings.

FIG. 5 is a call flow illustrating example methods for the management of teleconference calls.

DETAILED DESCRIPTION

Figure 1:
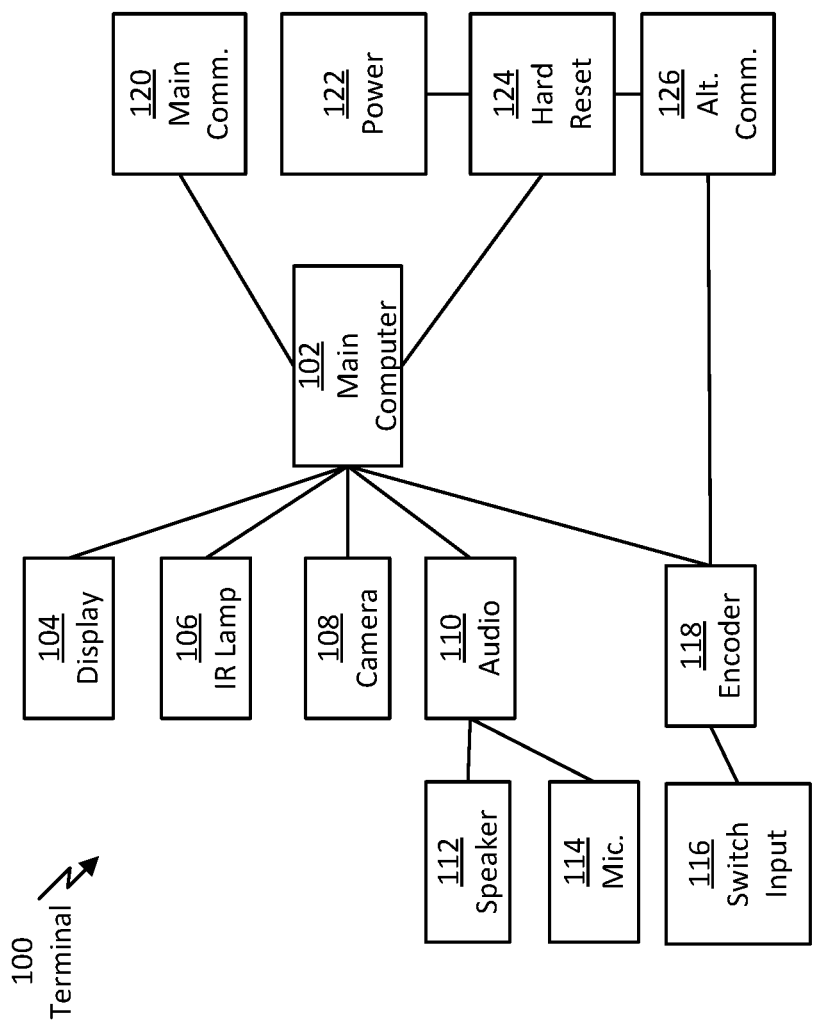
FIG. 1 is a block diagram of an example teleconference terminal.

FIG. 1 is a block diagram of an example video teleconferencing terminal 100. For brevity, herein the system is described in terms of its use in the context of providing secure teleconferencing to a medical treatment room. However, it will be appreciated that the techniques described herein may be equally applied in other circumstances calling for secure teleconferencing.

Terminal 100 may be used, for example, in a medical treatment room, such as an intensive care unit or acute care unit, to support teleconferencing of a remote clinician. Terminal 100 includes a main computer 102 which contains various operations and video display unit 104. A microphone 114 and speaker 112 are optionally supported by audio filtering, amplification, and digital/analog conversion circuitry 110. The microphone 114 may be a selective and/or a directional microphone, e.g., adapted to selectively receive input in a speech frequency range from a particular area in the vicinity of the terminal 100. Similarly, the speaker 112 may be chosen to optimize performance in the speech frequency range.

Terminal 100 includes a camera 108, which is optionally controlled by the main computer 102, e.g., via pan, tilt, and zoom instructions. Terminal 100 optionally includes an infrared (IR) lamp 106, and a camera 108. Camera 108 is optionally sensitive in the IR spectrum, to permit, e.g., nighttime or other low light observation of the vicinity of the terminal 100.

A switch input circuit 116 receives input from a switch, such as a momentary contact button switch, that is located in the treatment room, by which a user in the treatment room indicates a desire to initiate a teleconference. The switch input may be connected directly to the main computer 102 or via various communications circuitry to other systems. For example, in parallel to an input of the main computer 102, the switch input 116 may also be connected to a nurse station in proximity to the terminal 100. The switch input 116 may be connected to an encoder 118 which serves to optionally de-bounce the switch signal and/or encode a digital signal comprising an identifier of the switch, and then transmit the encoded signal to the main computer 102, local nurse station, or via alternative communication circuitry 126 to another system.

The main communication circuitry 120 may include a packet network interface, such as an Ethernet modem for wired, optical, or wireless connection to one or more IP protocol networks such as a LAN, WAN, or the Internet.

The components of terminal 100 may use a central power filtering, conditioning, conversion, and regulation circuit 122. A hard reset circuit 124 may be used to cycle power to reset conditions of operation of the components of terminal 100. The hard reset circuit 124 may be triggered, for example, by: detection of a power brown-out condition or glitch; a signal from the main computer; a local reset switch input; a remote reset switch input; a watchdog timer, e.g., triggered by the absence of a period signal from the main computer; and/or receipt of an external communications packet.

Terminal 100 may be a fixture in a room such as a medical treatment room. For example, terminal 100 may include an initial wall mounting plate which is affixed to a wall, and a set of encased modules that are then affixed to the wall mounting plate. The display 104 may be mounted on a pivot or articulated arm to allow adjustment of the viewing angle, where the pivot or arm is attached to a case or the wall mounting plate. Alternatively, terminal 100 may be mounted in a vehicle, e.g., an ambulance, or on a rolling cart.

Figure 2:
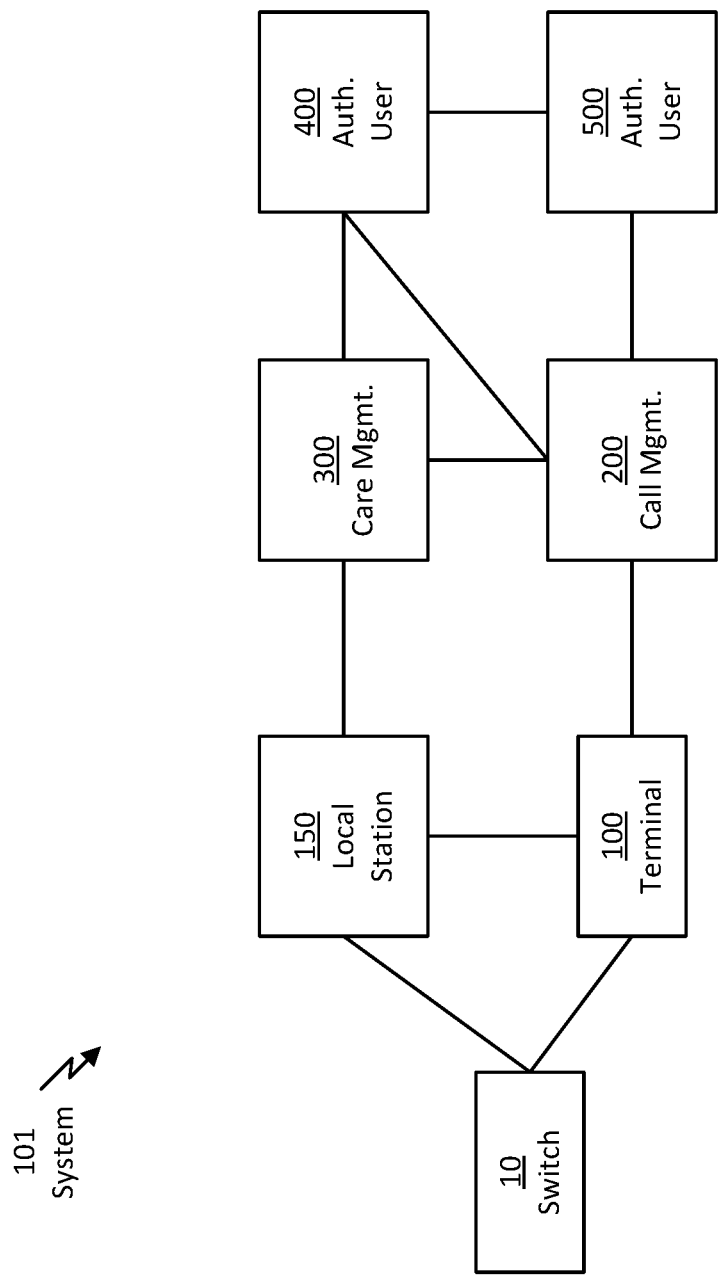
FIG. 2 is a block diagram of an example teleconference system.

FIG. 2 is a block diagram of an example teleconference system 101. A switch 10 is connected to the terminal 100, and optionally also connected to a local station 150. The local station 150 may be, for example, a nurse station near the terminal 100. The call management system 200 may be located on a remote server, or implemented, for example, as a cooperating distributed network of servers. The call management system 200 is used to coordinate and/or host teleconferencing calls. The call management system 200 is in communication with an authenticated user 400, and optionally in communication with an unauthenticated user 500.

Optionally, the teleconference system 101 is in communication with a care management system 300 which maintains records such as patient health records and medical sensor input data. In the teleconference system 101, the care management system 300 is separate and apart from the call management system 200. This permits the teleconference system 101 to provide teleconference call service without the terminal 100, call management system 200, authorized user 400, and unauthorized user 500 having any potentially sensitive patient information. For example, where the terminal is used in a medical treatment room, the systems involved in the teleconferencing call need not know the identity of the patient being treated or his condition, for example. For security purposes in case of breach or interception, it may be advantageous that these systems simply not store any such information, regardless of what data may be stored by the local station 150 or care management system 300.

Figure 3:
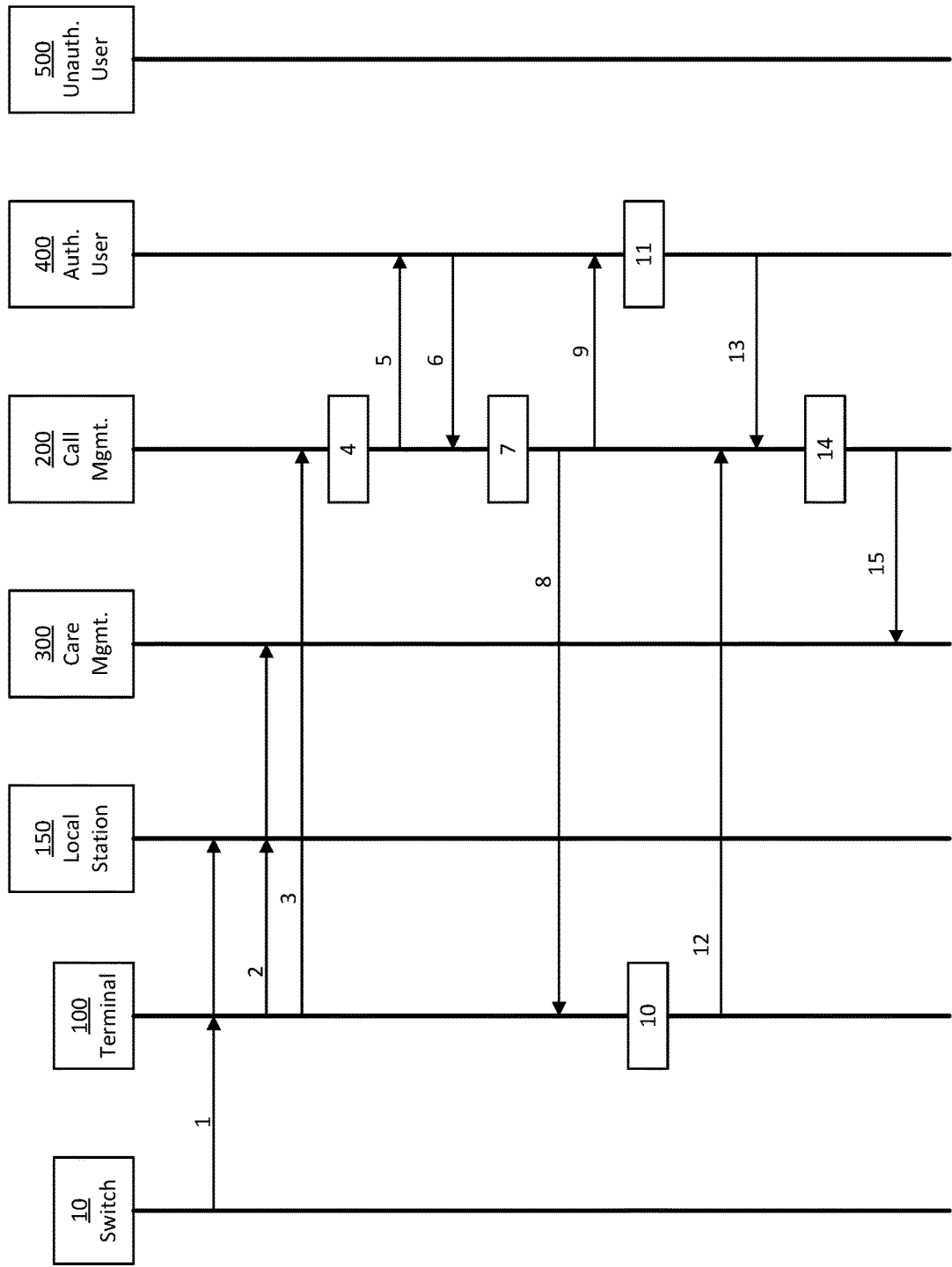
FIG. 3 is a call flow diagram of an example conference call initiated by a terminal.

FIG. 3 is a call flow of an example teleconference call initiated by terminal 100. The call is initiated by the pressing of the switch 10, which causes a switch signal 1 to be sent to the terminal 100, and optionally also sent to the local station 150. In this example, the local station 150 is alerted, but does not participate in the call. For information purposes, terminal 100 optionally sends an alert 2 of the request to the care management system 300 and/or local station 150. In this example, the care management system 300 does not participate in the call.

The terminal 100 sends a notice 3 of the request for a teleconference to the call management system 200. Notice 3 includes an identifier of terminal 100.

In step 4, the call management system 200 processes the notice 3 and, based on the identifier of terminal 100, selects one or more authenticated users to notify. For example, the call management system 200 may choose to notify a monitoring clinician, a backup monitoring clinician, and/or an attending physician about the notice 3.

The call management system 200 sends a notice 5 of the request to the authenticated user 400. In practice, the call management system 200 may send several such notices. For example, call management system 200 may send an electronic notification to a session to which the monitoring clinician is logged in, and also send a text message to the backup monitoring clinician, as well as an email to attending physician. Notice 5 may include a reference to the identity of terminal 100.

The authenticated user 400 responds with an affirmation 6 which indicates an intention to join a teleconference with terminal 100.

In step 7, the call management system 200 selects resources for the teleconference call. For example, the call management system 200 may identify system resources and establish a teleconference virtual meeting room. Alternatively, to expedite initiation of the call, the call management system may select one or more virtual meeting rooms from a pool of previously established virtual rooms which have not been used yet for any teleconference, for example.

In message 8, the call management system 200 informs the terminal 100 of any details required to join a teleconference, e.g., by providing a URL of a selected virtual meeting room. Similarly, in message 9, the call management system 200 informs the authenticated user of any details required to join the teleconference. Note that message 8 and message 9 may contain different information, e.g., where terminal 100 and the authenticated user 400 are served by different resources of a distributed network of cooperating servers within the call management system.

In step 10, using information provided by the call management system 200, the terminal 100 joins the teleconference. The teleconference may then be conducted using standard video teleconference protocols, for example. Terminal 100 may be adapted to join teleconferences only when the terminal 100 initiates the connection to a teleconference, such that no one may ever call into the terminal 100 for a teleconference. In other words, the terminal 100 may place calls, but will not answer calls. This provides security against unauthorized access, e.g., to the camera and microphone of the terminal 100.

Similarly, the information contained in message 8 and message 9 may be one-time-only use identifiers, such that only the first provider of such information will be connected to the associated teleconference, thus preventing improper use of intercepted information.

In step 11, the authenticated user 400 joins the teleconference using information provided by the call management system 200.

If optionally permitted, the terminal 100 may request termination of the teleconference by sending a message 12 to the call management system 200. This may be achieved, for example, by a second pressing of the switch 10. Similarly, the authenticated user 400 may request termination of the teleconference by sending a message 13 to the call management system 14.

In step 14, the call management system 200 determines when to terminate the teleconference. For example, the call management system 200 may determine to terminate the teleconference upon receipt of message 12 or message 13, or upon an observation of the loss of connection of one or more parties to the call, or upon the loss of system resources to support the call. To terminate the call, the call management system 200 disconnects any remaining parties to the call by, e.g., shutting down the virtual meeting room to which they are connected. For security reasons, it may be advantageous to destroy the virtual meeting room upon termination of teleconference, rendering all links to the virtual meeting room void.

Optionally, in step 14, the call management system may delete references to the virtual call room, e.g., such that the information provided in message 8 or message 9 cannot be used again, e.g., after improper interception of message 8 or message 9.

Not shown in FIG. 3, the authenticated user 400 may be permitted to join an unauthenticated user 500 to a teleconference call. For example, the authenticated user 400 may forward credentials included in message 9 to another party, e.g., a family member of a patient in the vicinity of terminal 100, or a clinical specialist not previously authenticated by the call management system 200. For example, a family member may join through a web browser on a PC or a mobile device from anywhere. Additionally or alternatively, the authenticated user 400 may request that call management system 200 provide the necessary credentials to the unauthenticated party 500.

In message 15, the call management system 200 may optionally report data regarding the teleconference to the care management system 300. For example, message 15 may describe the starting and ending times of the call or its length, how the call was initiated and terminated, and who attended the call.

Optionally, the local station 150 or care management system 300 may be permitted to join the teleconference, e.g., via audio only, or to receive a feed of the audio or video content thereof.

Figure 4:
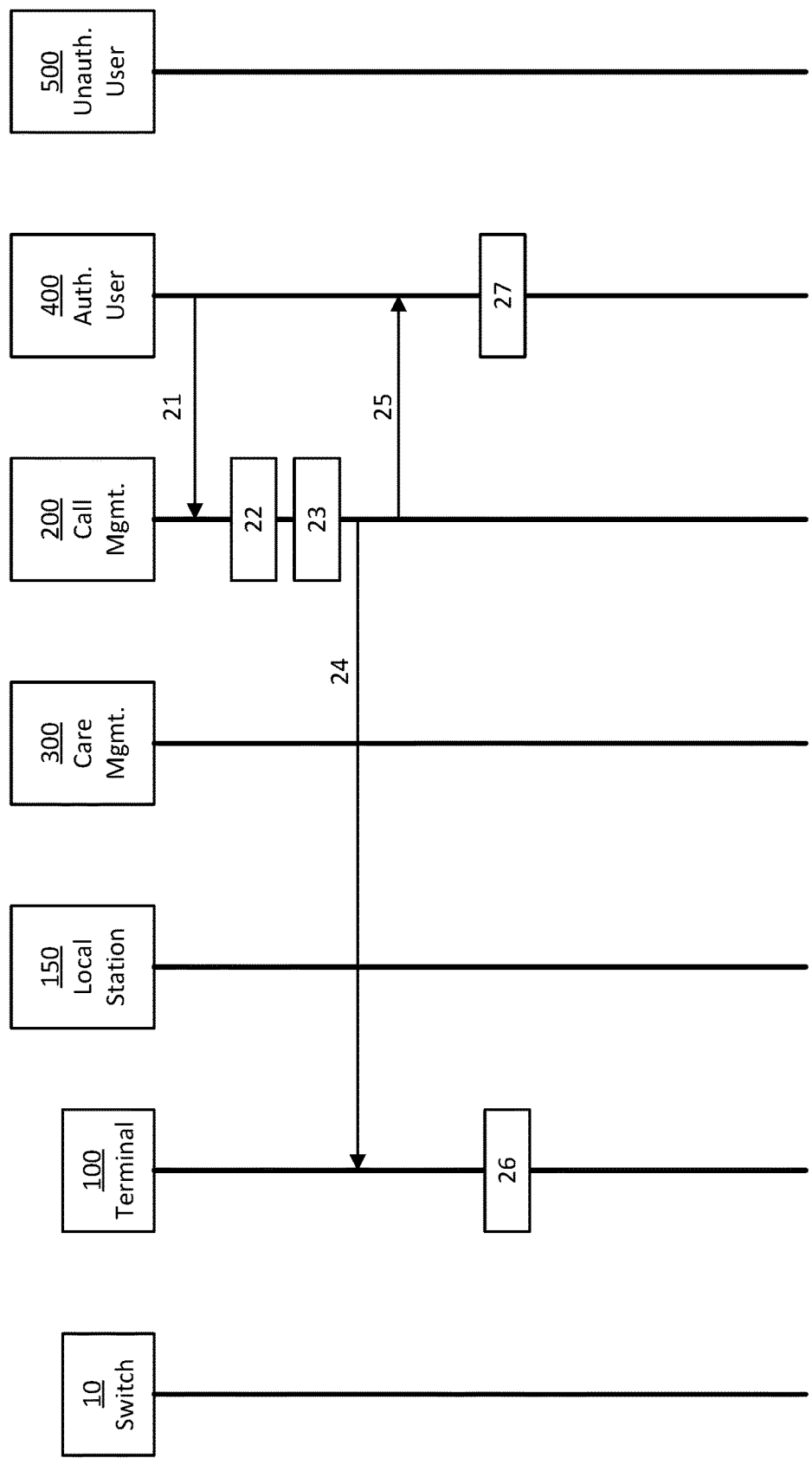
FIG. 4 is a call flow diagram of an example conference call initiated by a remote authenticated user.

FIG. 4 is a call flow of an example teleconference initiated by an authenticated user 400. For example, this method may be used when a monitoring clinician wishes to make an overnight observation of a patient in the vicinity of terminal 100. The authenticated user 400 sends a message 21 to the call management system 200, where message 21 includes an identifier of terminal 100. In step 22, the call management system 200 verifies that the authenticated user 400 is permitted to initiate a call with terminal 100. If permitted, in step 23 the call management system 200 then selects system resources for a teleconference. Again, this may include creating a new virtual meeting room or selecting a room from a pool of pre-established virtual meeting rooms, for example. The call management system then sends messages 24 and 25 to the terminal 100 and authenticated user 400, respectively, with information regarding joining a teleconference. Again, the information contained in messages 24 and 25 may be unique and distinct. In steps 26 and 27, the terminal 100 and authenticated user 400, respectively, are connected to a teleconference using information provided by the call management system. The call initiated in FIG. 4 may be terminated, e.g., the methods described in reference to FIG. 3.

Not shown in FIG. 4, the call management system 200 may optionally inform the care management system 300 of the request 21, decision 22, or details regarding any resulting teleconference.

FIG. 5 is a call flow illustrating a number of options for example teleconferences. In FIG. 5, entities are depicted in vertical boxes, and their interactions are drawn as arrows between the boxes. On the left, a clinician application is shown hosting a user, tech1@xyz.com. Beginning at the top left, the clinician application initiates a teleconference by requesting a directory lookup by a call policy server for the patient system in room 123. The patient system is a teleconference terminal. The call policy server, which is part of a call management system, responds by assigning virtual meeting room VMR456. The meeting room VMR456 may be selected from a pool of ready virtual meeting rooms. The client policy server informs the conference nodes to create VMR456, or alternatively alerts the conference nodes that a previously created virtual meeting room VMR456 is now reserved for a call. The clinician application then contacts the conference nodes requesting access to VMR456. The conference nodes verify the permissions of Tech 1 by contacting the client policy server. The conference nodes then setup the call with clinician application.

The client policy server then instructs the conference nodes to dial out to the room 123 by providing an identifier of the room, 789. That is, the patient system in room 123 is instructed to dial out to the assigned VMR. For security reasons, no dialing into the room is permitted. The patient system responds to start the call, and a connection to the teleconference is setup between the conference nodes and the patient system.

During the call, the clinician application issues a command to pan the camera in room 123. The camera commands are handled out of band of the teleconference. It is received by the call policy server, and forwarded as, e.g., a VISCA command to the pan/tilt/zoom (PTZ) function of the camera of the patient system. The camera subsystem acknowledges the command back to the call policy server.

Next, the clinician application requests to add another participant, Doctor 2, to the call. The request is received by the call policy server, which instructs the conference nodes to invite doctor 2 to the VMR 456 conference call. The conference nodes contact Doctor 2, who responds by setting up a connection to the call.

Similarly, the clinician application requests to add another participant, doctor 3, to the call via a web link. The client policy server receives the request, and provides web link information for inclusion back to the clinician application. The clinician application completes an email which it sends to the client policy server. The client policy server then sends the email/test to an SMTP address for doctor 3. Doctor 3 is then able to click on a web link included in the email/test, and setup a connection to VMR 456 by contacting the conference nodes.

At some point, the clinician application terminates the teleconference by sending a request to end the call to the conference nodes. The conference nodes may then send call termination notices to, e.g., the patient system, doctor 2, and doctor 3. The conference nodes also inform the call policy server that the call has ended. The call policy server then instructs the conference nodes to delete VMR 456.

A user may initiate a change in pan, tilt, and zoom position to highlight a specific location in a room by, for example, clicking and holding a mouse button when pointing the mouse to a specific location of a room shown in a teleconference image of the room. This may be achieved with precision, for example, through the use of gnomonic projection principles. A gnomonic transformation from the current camera position to the desired camera position may begin with recording the location indicated by the mouse click and the starting pan, tilt, and zoom position of the camera at the time of the mouse click. From the current position, the current field of view of the camera may be inferred.

Gnomonic projection principles may then be used to determine absolute pan and tilt values of a selected location, and the determined pan and tilt values may then be used for instructing a camera to move from the current field of view to a new view selected. For example, a new view may be centered on centered on a point selected by a click on a pixel or small region of the current two-dimensional view. Starting with the starting pan/tilt position of the camera, and the destination (x, y) coordinates from the camera image, a gnomonic projection algorithm may be used to provide the absolute pan/tilt coordinates that will center the camera on those the selected x/y coordinates to enable precise zoom operation.

Specifically, an inverse gnomonic transformation may be used. Inherently, a traditional camera lens creates a gnomonic projection—a flattened image of the field of view of the camera, where the field of view is a function of the pan, tilt, and zoom settings at the time the image is made. Put another way, a standard, rectilinear lens, e.g., as opposed to a pin-hole or fish-eye lens, will produce an image where straight features in the observed space are seen as straight lines in the produced image. The image will be predictably warped according to a gnomonic projection pattern. An inverse gnomonic transformation may be used to infer the new pan and tilt settings to center a new image on the (x, y) coordinates selected on a given image. The new pan and tilt settings may then be sent to the camera.

A variety of methods may be used to determine the zoom setting. For example, in providing a click-to-center-and zoom function, the new zoom may be set as a fixed increment higher, a fixed percent higher, or a percentage of remaining zoom capacity higher.

A variety of methods may be used to enhance the user's experience of a click-to-center-and zoom function. For example, the sequence of panning, tilting, and zooming may be selected to avoid disorientation of the user. For example, panning and tilting may be set to occur first, so that the user can observe the movement of the center of the field view at the current zoom, and then zooming occurs after the image is re-centered. Similarly, the rate of panning, tilting, and zooming may be set to occur at certain rates, e.g., as determined as a function of the current zoom level.

In performing a gnomonic transformation, it may be advantageous to use a calibration in determining an initial field of view. The field of view is a property of a given camera lens and its zoom level. Thus, the inputs to a gnomic transformation algorithm may include, in addition to the starting pan/tilt position, the starting zoom level and camera model, or calibration data associated therewith. For example, a calibration table may be used to look up the field of view expected for a zoom level for a specific camera or for a model of camera.

Unfortunately, camera manufacturers may not provide sufficient information to extrapolate such a calibration table. A camera may have thousands of zoom positions, and a gnomonic transformation may require an accurate initial field of view input. Therefore, it may be create a field of view calibration table via rigorous physical testing of a camera's actual field of view as a function, for example, of its PTZ settings. A calibration may be stored, for example, as set of such observed numerical data.

Alternatively, a calibration table may be stored as a set of polynomial expressions corresponding to the observed field of view data. For example, a polynomial derivation may be conducted on raw field of view test data obtained for a camera, and, separately, the resulting polynomial expressions may then be used during a video teleconference to facilitate a gnomonic transformation.

It will be appreciated that the methods described herein may be applied in a number of sequences. The steps need not necessarily be performed in the exact sequence given in the examples to achieve the described results.

It will be further appreciated that the methods and apparatuses described herein may be used in a variety of situations calling for securing teleconferencing, such as, but not limited to: observation of nursing facilities, holding cells, laboratories, or zoological exhibits; e-sitting, baby-sitting, or home nursing observation; clinical interventions in the home; psychiatric observation; and emergency clinical interventions.

It is understood that any or all of the systems, methods and processes described herein may be embodied in the form of computer executable instructions (i.e., program code) stored on a computer-readable storage medium which instructions, when executed by a machine, such as an apparatus of a digital protocol network, including for example a secure terminal, a server, gateway, mobile device or the like, perform and/or implement the systems, methods and processes described herein. Specifically, any of the steps, operations or functions described above may be implemented in the form of such computer executable instructions. Computer readable storage media include both volatile and nonvolatile, removable and non-removable media implemented in any non-transitory (i.e., tangible or physical) method or technology for storage of information, but such computer readable storage media do not includes signals. Computer readable storage media include, but are not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other tangible or physical medium which may be used to store the desired information and which may be accessed by a computer.

We claim:

1. A method performed by a call management system, comprising:
    receiving, a teleconference initiation request, the teleconference initiation request pertaining to initiating a teleconference;
    identifying a virtual meeting room for the teleconference;
    sending, to a secure terminal, details required to join the teleconference, wherein the secure terminal is configured to not allow any incoming conference calls;
    receiving, from the secure terminal, a call, the call identifying the teleconference; and
    joining the secure terminal to the teleconference in the virtual meeting room.

2. The method of claim 1, further comprising:
    maintaining a pool of unused virtual meeting rooms;
    selecting the virtual meeting room from the pool of unused virtual meeting rooms; and
    removing, upon initiation of the teleconference, the virtual meeting room from the pool of unused virtual meeting rooms.

3. The method of claim 2, further comprising, upon termination of the teleconference, deleting the virtual meeting room.

4. The method of claim 3, further comprising:
    identifying an authenticated user, the authenticated user being associated with the secure terminal;
    sending, to the authenticated user, details required to join the teleconference;
    receiving, from the authenticated user, a first join request, the first join request indicating the teleconference; and
    joining the authenticated user to the teleconference in the virtual meeting room.

5. The method of claim 4, further comprising:
    sending, to an unauthorized user, details required to join the teleconference;
    receiving, from the unauthorized user, a second join request, the second join request indicating the teleconference; and
    joining the unauthorized user to the teleconference in the virtual meeting room.

6. The method of claim 5, wherein the teleconference initiation request is received from the secure terminal.

7. The method of claim 6, wherein the teleconference initiation request pertains to a switch input signal, the switch input signal occurring at a switch affixed to or connected to the secure terminal, the switch input signal indicating an intention to initiate the teleconference.

8. The method of claim 7, further comprising encoding and sending, to a station associated with the secure terminal, a notification of the teleconference initiation request.

9. The method of claim 6, further comprising selecting the unauthorized user on the basis of a preconfigured setting associated with the secure terminal.

10. The method of claim 9, further comprising:
    receiving, from the authenticated user, a caller add request, the caller add request indicating the unauthorized user; and
    selecting the unauthorized user on the basis of the caller add request.

11. The method of claim 5, wherein the teleconference initiation request is received from the authenticated user.

12. The method of claim 11, further comprising selecting the unauthorized user on the basis of a preconfigured setting associated with the secure terminal.

13. The method of claim 11, further comprising:
    receiving, from the authenticated user, a caller add request, the caller add request indicating the unauthorized user; and
    selecting the unauthorized user on the basis of the caller add request.

14. The method of claim 13, further comprising providing, to the authenticated user, a list of unauthorized users, the list of unauthorized users being associated with the secure terminal, wherein the unauthorized user is selected from the list of unauthorized users.

15. The method of claim 5, further comprising:
    receiving, from the authenticated user, a selection of a target area for enlargement within a two-dimensional teleconference image;
    determining a three-dimensional coordinate of the selected target area; and
    sending, to the secure terminal, a set of camera instructions based on the three dimensional coordinate.

16. The method of claim 15, wherein determining the three dimensional coordinate of the selected target area is achieved via an inverse gnomonic transformation of one or more X, Y coordinates of the selected target area.

17. The method of claim 16, further comprising determining one or more X, Y coordinates of the selected target area by detecting a user holding a mouse click at a point on the two-dimensional teleconference image.

18. The method of claim 16, wherein the set of camera instructions comprises changes to a zoom level of the camera.

19. The method of claim 16, wherein the set of camera instructions comprises a rate at which to change a pan, a tilt, or a zoom.

20. The method of claim 15, wherein the set of camera instructions is sent out of band of the teleconference.

* * * * *

UNITED STATES PATENT AND TRADEMARK OFFICE
CERTIFICATE OF CORRECTION

| | |
|---|---|
| PATENT NO. | : 11,134,218 B2 |
| APPLICATION NO. | : 17/072161 |
| DATED | : September 28, 2021 |
| INVENTOR(S) | : John Mitchell Vitale et al. |

It is certified that error appears in the above-identified patent and that said Letters Patent is hereby corrected as shown below:

On the Title Page

Item (63), Line 2: delete "10,545,713" and insert --10,848,713--.

Signed and Sealed this
Twenty-second Day of August, 2023

Katherine Kelly Vidal
*Director of the United States Patent and Trademark Office*